United States Patent
Pansiera et al.

(10) Patent No.: US 8,715,367 B1
(45) Date of Patent: May 6, 2014

(54) APPARATUS AND METHOD FOR AN ORTHOTIC AND PROSTHETIC JOINT

(75) Inventors: Timothy T. Pansiera, Cortez, FL (US);
David Lee Stubbers, Bradenton, FL (US)

(73) Assignee: Fillauer Companies, Inc., Chattanooga, TN (US)

( * ) Notice: Subject to any disclaimer, the term of this patent is extended or adjusted under 35 U.S.C. 154(b) by 165 days.

(21) Appl. No.: 13/493,526

(22) Filed: Jun. 11, 2012

Related U.S. Application Data

(60) Provisional application No. 61/520,537, filed on Jun. 10, 2011.

(51) Int. Cl.
*A61F 2/64* (2006.01)
*A61F 5/00* (2006.01)

(52) U.S. Cl.
USPC .............................................. 623/43; 623/59

(58) Field of Classification Search
CPC .................................... A61F 2/64; A61F 5/00
USPC ....................... 623/43, 59, 60; 602/16, 20, 26
See application file for complete search history.

(56) References Cited

U.S. PATENT DOCUMENTS

| | | | | |
|---|---|---|---|---|
| 2,812,961 A | * | 11/1957 | Brown et al. | 403/93 |
| 5,314,500 A | * | 5/1994 | Weddendorf | 623/57 |
| 7,935,153 B2 | * | 5/2011 | Auberger | 623/43 |
| 8,591,444 B2 | * | 11/2013 | Bejarano et al. | 602/16 |

\* cited by examiner

*Primary Examiner* — Bruce E Snow
(74) *Attorney, Agent, or Firm* — Chambliss, Bahner & Stophel, P.C.

(57) ABSTRACT

The apparatus of the invention comprises a mechanical joint that is adapted for use on a user's anatomical joint which has a proximal area, a distal area, a lateral side and a medial side. The preferred mechanical joint comprises a proximal body that is disposed adjacent to the proximal area of the user's anatomical joint and a distal race that is disposed adjacent to the distal area of the user's anatomical joint. The preferred mechanical joint also comprises a release plate, an iris, a roller bearing pin, a resilient tube and a drive pin that are substantially disposed in the proximal body. The preferred mechanical joint further comprises a pivot screw that is adapted to pivotally connect the proximal body and the distal race and a cable pull assembly that is adapted to permit the distal race and the proximal body to move relative to each other.

20 Claims, 10 Drawing Sheets

APPARATUS AND METHOD FOR AN ORTHOTIC AND PROSTHETIC JOINT

CROSS-REFERENCES TO RELATED APPLICATIONS/PATENTS

This application relates back to and claims priority from U.S. Provisional Application for Patent No. 61/520,537 of Pansiera titled "Apparatus and Method for an Orthotic and Prosthetic Joint" and filed on Jun. 10, 2011.

FIELD OF THE INVENTION

The present invention relates generally to orthotic and prosthetic joints, and particularly to orthotic knee joints.

BACKGROUND AND DESCRIPTION OF THE PRIOR ART

It is known to use cam locks or sprag-type bearings in orthotic and prosthetic joints. Conventional joints, however, suffer from one or more disadvantages. For example, conventional joints are undesirably heavy and large. Conventional joints also do not demonstrate optimal performance or functionality. More particularly, the mechanical release mechanisms of conventional joints have an undesirably long distance to travel and standard sprag bearings must be coupled with an external release mechanism such as a ratcheting device. Further, conventional joints are not cosmetically pleasing. Still further, conventional joints do not permit the user to wear them on both sides of the user's anatomical joint, e.g. the lateral and medial sides of the user's anatomical knee joint. In addition, conventional joints are undesirably complex and costly to manufacture, repair and maintain. Conventional joints are also undesirably noisy and do not have sufficiently narrow profiles.

It would be desirable, therefore, if an apparatus and method for an orthotic and prosthetic joint could be provided that would be lighter and smaller than conventional joints. It would also be desirable if such an apparatus and method for an orthotic and prosthetic joint could be provided that would demonstrate improved performance and functionality as compared to conventional joints. More particularly, it would be desirable if the distance travelled by the release mechanism could be reduced and an external release mechanism such as a ratcheting device could be eliminated. It would be further desirable if such an apparatus and method for an orthotic and prosthetic joint could be provided that would be more cosmetically pleasing than conventional joints. It would be still further desirable if such apparatus and method for an orthotic and prosthetic joint could be provided that would permit the user to wear the joint on both sides of the user's anatomical joint, e.g. the lateral and medial sides of the user's anatomical knee joint. In addition, it would be desirable if such an apparatus and method for an orthotic and prosthetic joint could be provided that would be simpler and less costly to manufacture, repair and maintain. It would also be desirable if such an apparatus and method for an orthotic and prosthetic joint could be provided that would reduce or eliminate noise during use and reduce the profile of the joint.

ADVANTAGES OF THE PREFERRED EMBODIMENTS OF THE INVENTION

Accordingly, it is an advantage of the preferred embodiments of the invention claimed herein to provide an apparatus and a method for an orthotic and prosthetic joint that is lighter in weight and smaller in size. It is also an advantage of the preferred embodiments of the invention claimed herein to provide such an apparatus and a method that demonstrates improved performance and functionality. More particularly, it is an advantage of the preferred embodiments of the invention claimed herein to provide an apparatus and a method for an orthotic and prosthetic joint having a release mechanism that travels a shorter distance than conventional joints and requires no external release mechanism such as a ratcheting device. It is a further advantage of the preferred embodiments of the invention claimed herein to provide such an apparatus and a method that is more cosmetically pleasing than conventional joints. It is a still further advantage of the preferred embodiments of the invention claimed herein to provide such an apparatus and method that permits the user to wear the joint on both sides of the user's anatomical joint, e.g. the lateral and medial sides of the user's anatomical knee joint. It is also an advantage of the preferred embodiments of the invention claimed herein to provide such an apparatus and method that reduces or eliminates noise during operation and reduces the profile of the joint.

Additional advantages of the preferred embodiments of the invention will become apparent from an examination of the drawings and the ensuing description.

SUMMARY OF THE INVENTION

The apparatus of the invention comprises a mechanical joint that is adapted for use on a user's anatomical joint which has a proximal area, a distal area, a lateral side and a medial side. The preferred mechanical joint comprises a proximal body that is disposed adjacent to the proximal area of the user's anatomical joint and a distal race that is disposed adjacent to the distal area of the user's anatomical joint. The preferred mechanical joint also comprises a release plate that is substantially disposed in the proximal body, an iris that is substantially disposed in the proximal body, a roller bearing pin that is substantially disposed in the proximal body, a resilient tube that is substantially disposed in the proximal body and a drive pin that is substantially disposed in the proximal body. The preferred mechanical joint further comprises a pivot screw that is adapted to pivotally connect the proximal body and the distal race and a cable pull assembly that is adapted to permit the distal race and the proximal body to move relative to each other.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS OF THE INVENTION

Figure 1:
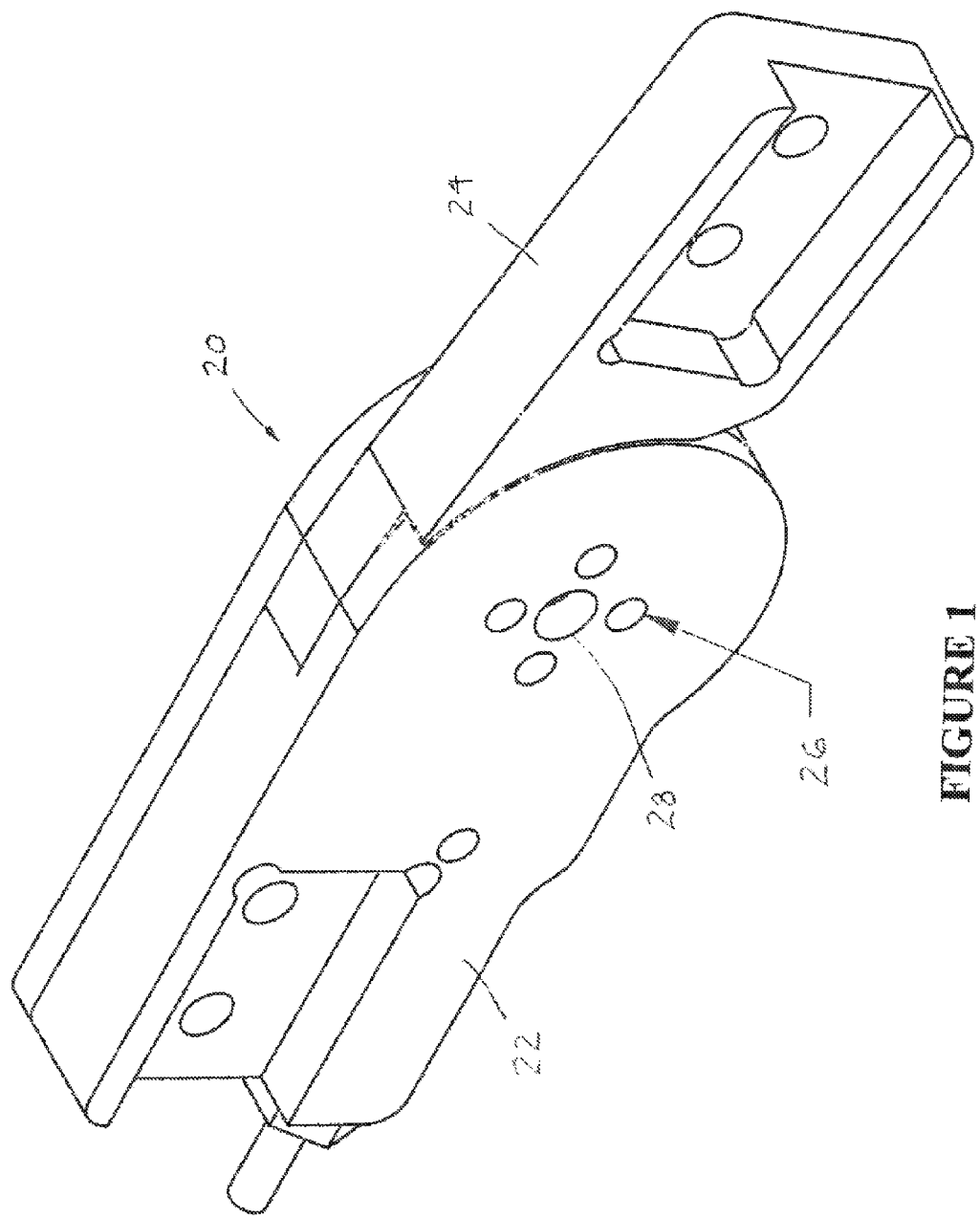
FIG. 1 is a perspective front view of the preferred embodiment of the mechanical joint in accordance with the present invention.

Referring now to the drawings, the preferred embodiment of the mechanical joint in accordance with the present invention is illustrated by FIGS. 1 through 10. As shown in FIGS. 1-10, the preferred mechanical joint is adapted to provide an apparatus and a method for an orthotic and prosthetic joint that is lighter in weight and smaller in size. The preferred embodiments of the invention also provide an apparatus and a method that demonstrates improved performance and functionality. More particularly, the preferred embodiments of the invention provide an apparatus and a method for an orthotic and prosthetic joint having a release mechanism that travels a shorter distance than conventional joints and requires no external release mechanism such as a ratcheting device. The preferred embodiments of the invention provide an apparatus and a method that is more cosmetically pleasing than conventional joints. The preferred embodiments of the invention also provide an apparatus and method that permits the user to wear the joint on both sides of the user's anatomical joint, e.g. the lateral and medial sides of the user's anatomical knee joint. Further, the preferred embodiments of the invention provide an apparatus and method that reduces or eliminates noise during operation and reduces the profile of the mechanical joint.

Referring now to FIG. 1, a perspective front view of the preferred embodiment of the mechanical joint in accordance with the present invention is illustrated. As shown in FIG. 1, the preferred mechanical joint is designated generally by reference numeral 20. The preferred mechanical joint 20 is adapted for use on a user's anatomical joint. The user's anatomical joint has a proximal area, a distal area, a lateral side and a medial side. The preferred mechanical joint 20 comprises proximal body 22. The preferred proximal body 22 is adapted to be disposed adjacent to the proximal area of the user's anatomical joint. The preferred mechanical joint 20 also comprises distal race 24. The preferred distal race 24 is adapted to be disposed adjacent to the distal area of the user's anatomical joint. The preferred mechanical joint 20 also comprises drive pin holes 26 which are adapted to receive drive pins. The preferred mechanical joint 20 further comprises a pivot screw hole 28 which is adapted to receive a pivot screw. The preferred pivot screw hole 28 also defines the pivot point about which proximal body 22 and distal race 24 move relative to each other.

Still referring to FIG. 1, the preferred mechanical joint 20 has a narrow profile. More particularly, the preferred mechanical joint 20 has a profile that is approximately 0.5". In addition, the preferred mechanical joint 20 may be worn on either the lateral or medial side of the user's joint or on both sides simultaneously. While FIG. 1 illustrates the preferred configuration and arrangement of the mechanical joint in accordance with the present invention, it is contemplated within the scope of the invention that the mechanical joint may be of any suitable arrangement or configuration.

Figure 2:
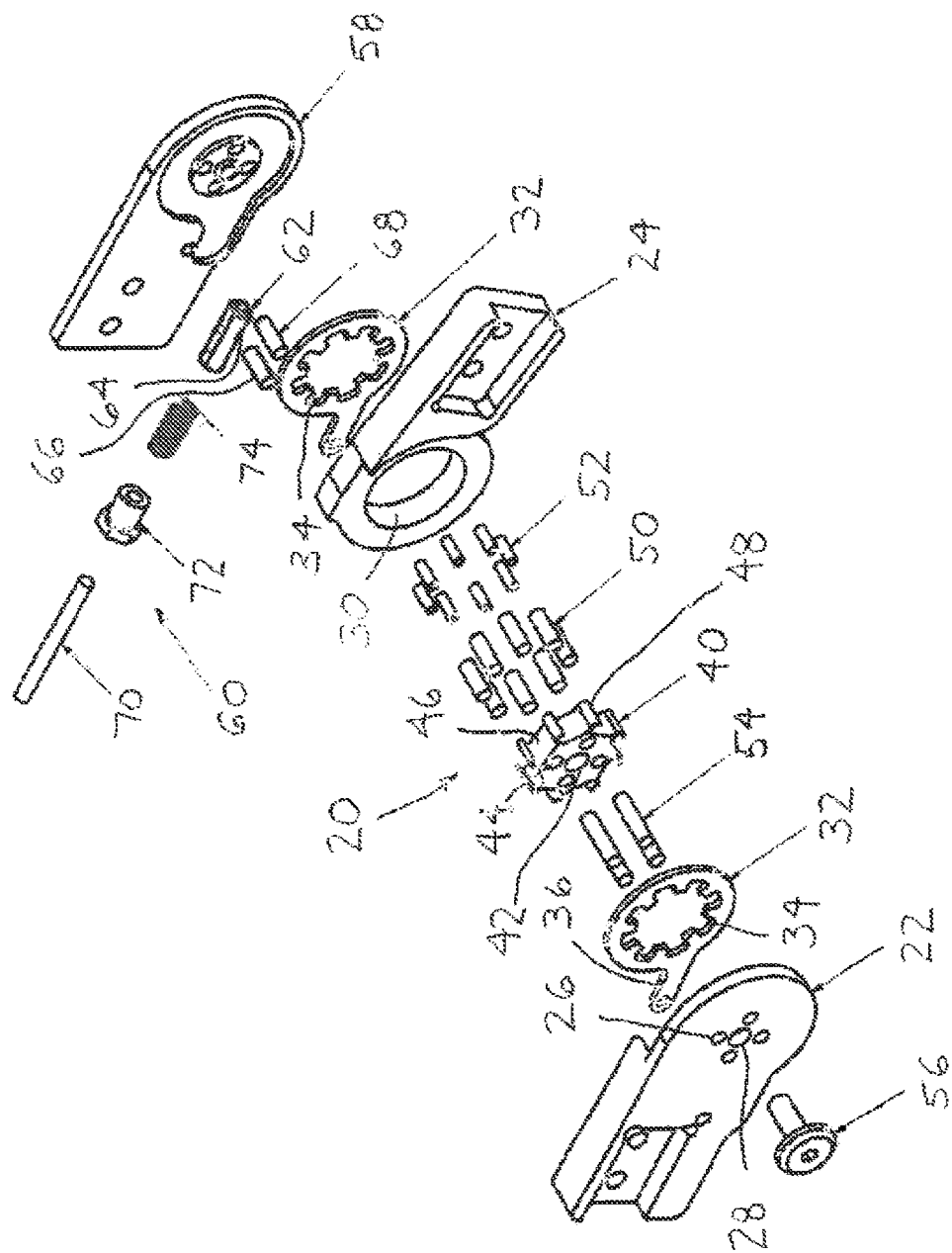
FIG. 2 is an exploded perspective front view of the preferred embodiment of the mechanical joint illustrated in FIG. 1.

Referring now to FIG. 2, an exploded perspective front view of preferred mechanical joint 20 is illustrated. As shown in FIG. 2, preferred mechanical joint 20 comprises proximal body 22, distal race 24, drive pin holes 26 and pivot screw hole 28. The preferred distal race 24 comprises round race 30. The preferred mechanical joint 20 also comprises release plates 32 which are substantially disposed in proximal body 22. The preferred release plates 32 include a plurality of notches 34 and a release plate arm 36. The preferred release plates are adapted to rotate within proximal body 22. The preferred mechanical joint 20 further comprises iris 40 which is substantially disposed in proximal body 22. The preferred iris 40 includes pivot screw aperture 42, drive pin holes 44, roller ramps 46 and roller pockets 48. The preferred roller ramps 46 slope inwardly toward roller pockets 48. The preferred mechanical joint 20 still further comprises roller bearing pins 50 which are substantially disposed in proximal body 22. The preferred roller bearing pins 50 are adapted to be received on the roller ramps of iris 40. In addition, the preferred mechanical joint 20 comprises resilient tubes 52 which are substantially disposed in proximal body 22. The preferred resilient tubes 52 are adapted to be received on the roller ramps of iris 40 and bear against roller bearing pins 50. The preferred mechanical joint 20 also comprises drive pins 54 which are substantially disposed in proximal body 22. The preferred drive pins 54 are adapted to prevent the rotational movement of iris 40. The preferred mechanical joint 20 further comprises pivot screw 56 which is adapted to pivotally connect proximal body 22 and distal race 24. The preferred mechanical joint 20 still further comprises proximal plate 58 which is disposed adjacent to proximal body 22.

Still referring to FIG. 2, the preferred mechanical joint 20 further comprises cable pull assembly 60 which is adapted to permit distal race 24 and proximal body 22 to move relative to each other. The preferred cable pull assembly 60 comprises cable pull actuator 62. The preferred cable pull actuator 62 comprises actuator ramp 64. The preferred cable pull assembly 60 also comprises cable pull pin 66 which is adapted to bear against actuator 62 and actuator pin 68 which is adapted to bear against actuator ramp 64. The preferred cable pull assembly 60 also comprises cable pull connector 70, guide screw 72 and return spring 74. The preferred cable pull assembly 60 is adapted to rotate release plates 32. While FIG. 2 illustrates the preferred configuration and arrangement of the mechanical joint in accordance with the present invention, it is contemplated within the scope of the invention that the mechanical joint may be of any suitable configuration or arrangement. It is also contemplated within the scope of the invention that the cable pull assembly comprises an electro-mechanical cable system.

Figure 3:
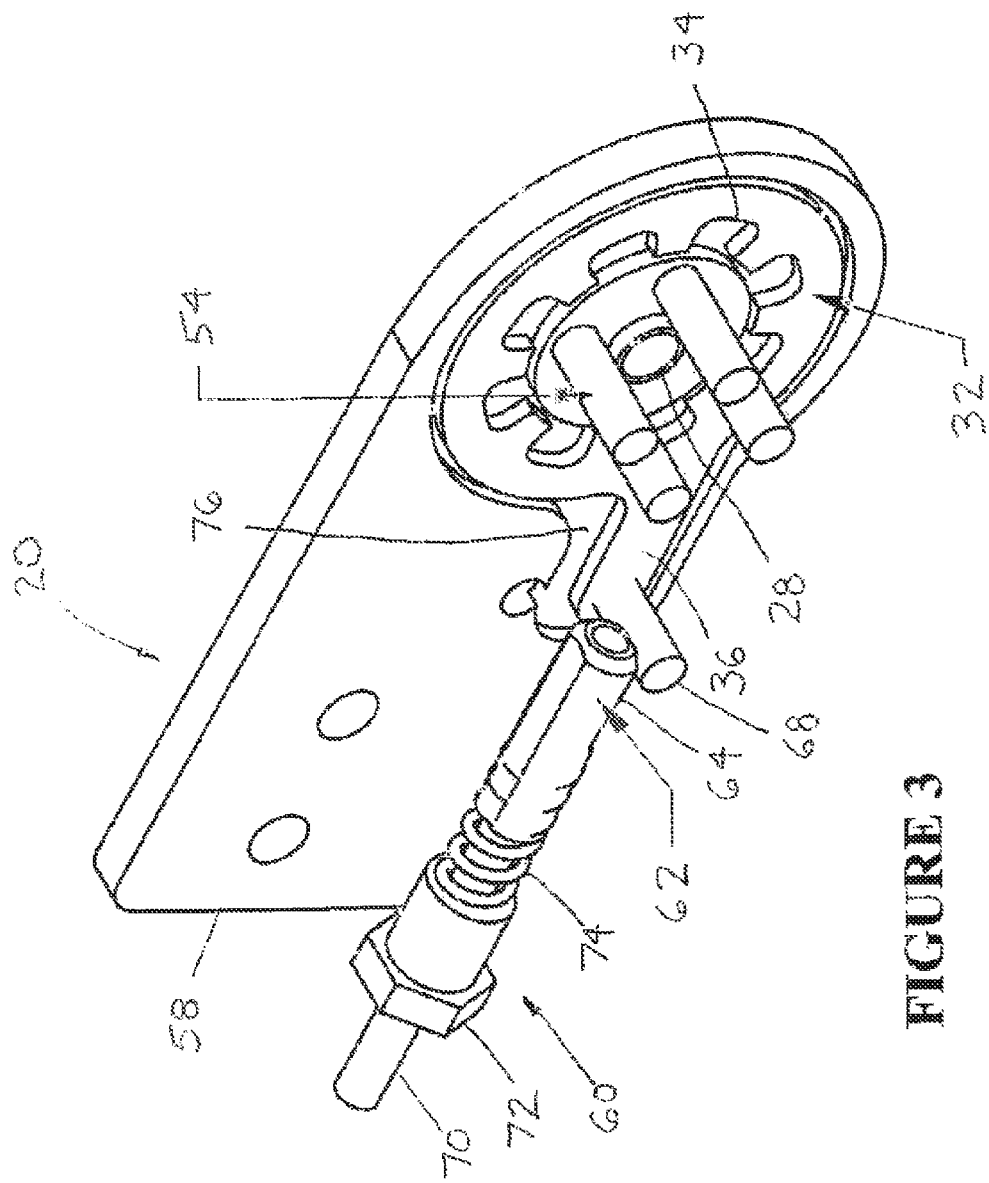
FIG. 3 is a perspective front view of the preferred embodiment of the mechanical joint illustrated in FIGS. 1 and 2.

Referring now to FIG. 3, a perspective front view of the preferred mechanical joint 20 is illustrated. As shown in FIG. 3, the preferred mechanical joint 20 comprises pivot screw hole 28, release plate 32, release plate notches 34, release plate arm 36, drive pins 54, proximal plate 58, and cable pull assembly 60. The preferred cable pull assembly 60 comprises cable pull actuator 62, actuator ramp 64, actuator pin 68, cable pull connector 70, guide screw 72 and return spring 74. As shown in FIG. 3, preferred release plate 32 is disposed in pocket 76 of proximal plate 58.

Figure 4:
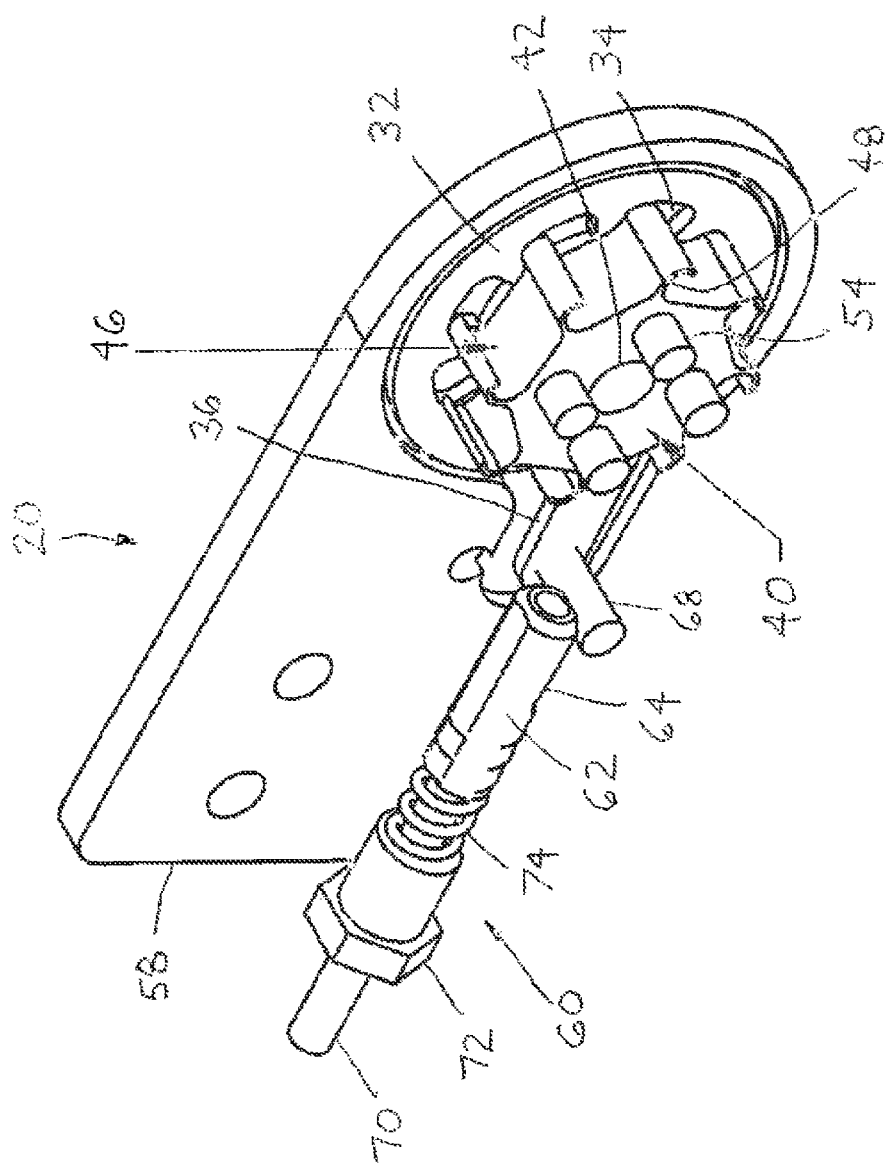
FIG. 4 is a perspective front view of the preferred embodiment of the mechanical joint illustrated in FIGS. 1 through 3.

Referring now to FIG. 4, a perspective front view of the preferred mechanical joint 20 is illustrated. As shown in FIG. 4, the preferred mechanical joint 20 comprises release plate 32, release plate notches 34, release plate arm 36, iris 40, pivot screw aperture 42, roller ramps 46, roller pockets 48, drive pins 54, proximal plate 58, and cable pull assembly 60. The preferred cable pull assembly 60 comprises cable pull actuator 62, actuator ramp 64, actuator pin 68, cable pull connector 70, guide screw 72 and return spring 74.

Figure 5:
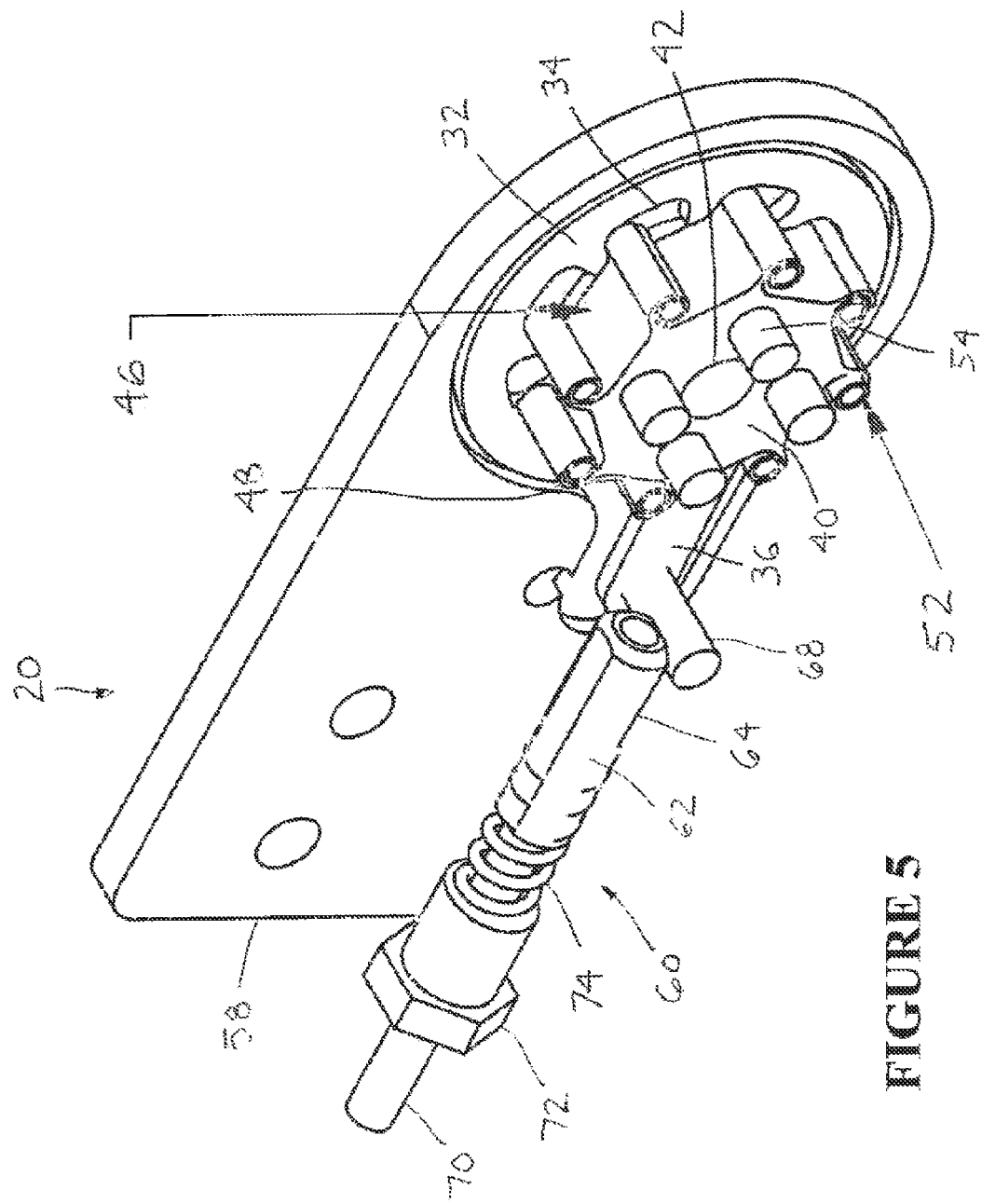
FIG. 5 is a perspective front view of the preferred embodiment of the mechanical joint illustrated in FIGS. 1 through 4.

Referring now to FIG. 5, a perspective front view of the preferred mechanical joint 20 is illustrated. As shown in FIG. 5, the preferred mechanical joint 20 comprises release plate 32, release plate notches 34, release plate arm 36, iris 40, pivot screw aperture 42, roller ramps 46, roller pockets 48, resilient tubes 52, drive pins 54, proximal plate 58, and cable pull assembly 60. The preferred cable pull assembly 60 comprises cable pull actuator 62, actuator ramp 64, actuator pin 68, cable pull connector 70, guide screw 72 and return spring 74.

Figure 6:
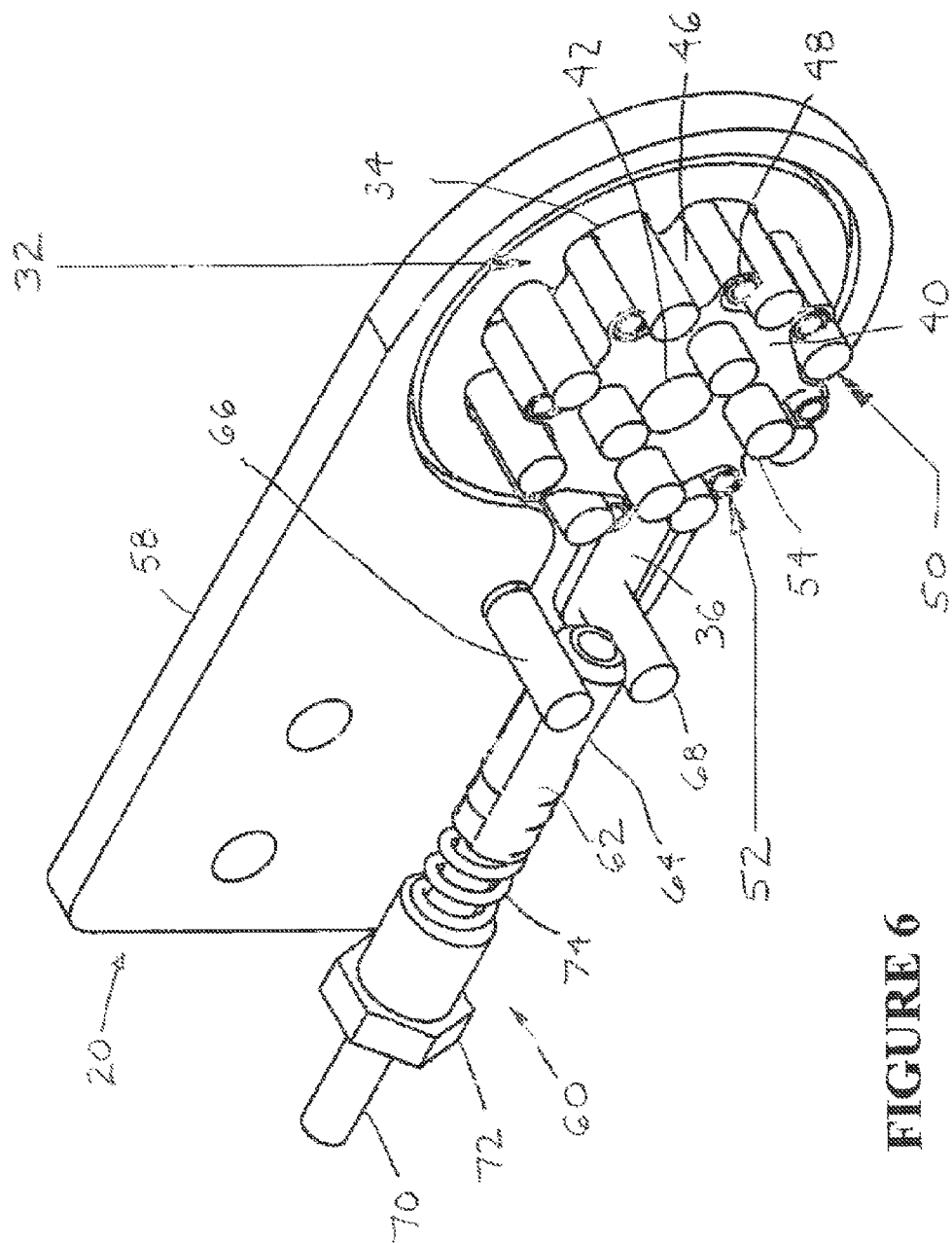
FIG. 6 is a perspective front view of the preferred embodiment of the mechanical joint illustrated in FIGS. 1 through 5.

Referring now to FIG. 6, a perspective front view of the preferred mechanical joint 20 is illustrated. As shown in FIG. 6, the preferred mechanical joint 20 comprises release plate 32, release plate notches 34, release plate arm 36, iris 40, pivot screw aperture 42, roller ramps 46, roller pockets 48, roller hearing pins 50, resilient tubes 52, drive pins 54, proximal plate 58, and cable pull assembly 60. The preferred cable pull assembly 60 comprises cable pull actuator 62, actuator ramp 64, cable pull pin 66, actuator pin 68, cable pull connector 70, guide screw 72 and return spring 74.

Figure 7:
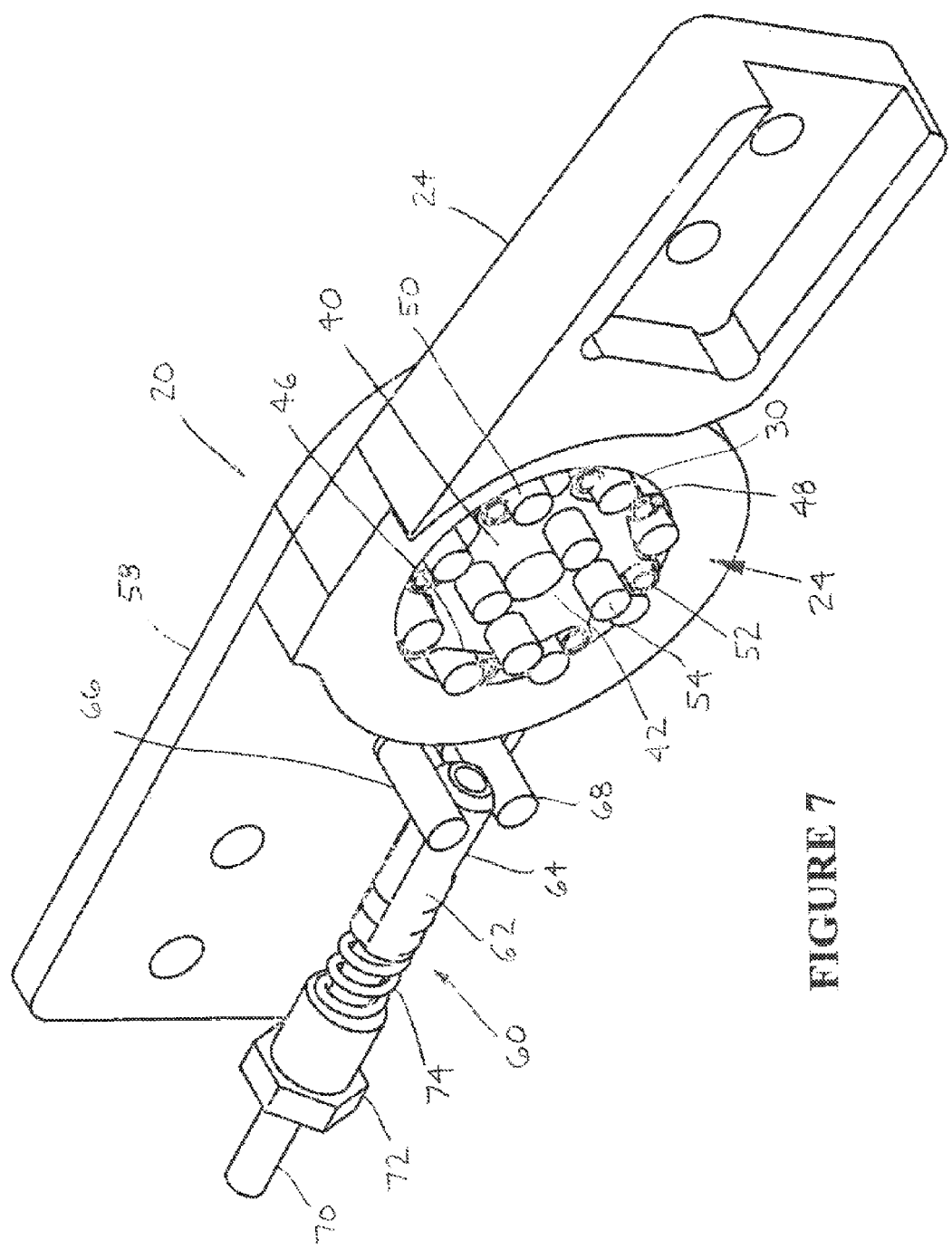
FIG. 7 is a perspective front view of the preferred embodiment of the mechanical joint illustrated in FIGS. 1 through 6.

Referring now to FIG. 7, a perspective front view of the preferred mechanical joint 20 is illustrated. As shown in FIG. 7, the preferred mechanical joint 20 comprises distal race 24, iris 40, pivot screw aperture 42, roller ramps 46, roller pockets 48, roller hearing pins 50, resilient tubes 52, drive pins 54, proximal plate 58, and cable pull assembly 60. The preferred cable pull assembly 60 comprises cable pull actuator 62, actuator ramp 64, cable pull pin 66, actuator pin 68, cable pull connector 70, guide screw 72 and return spring 74.

Figure 8:
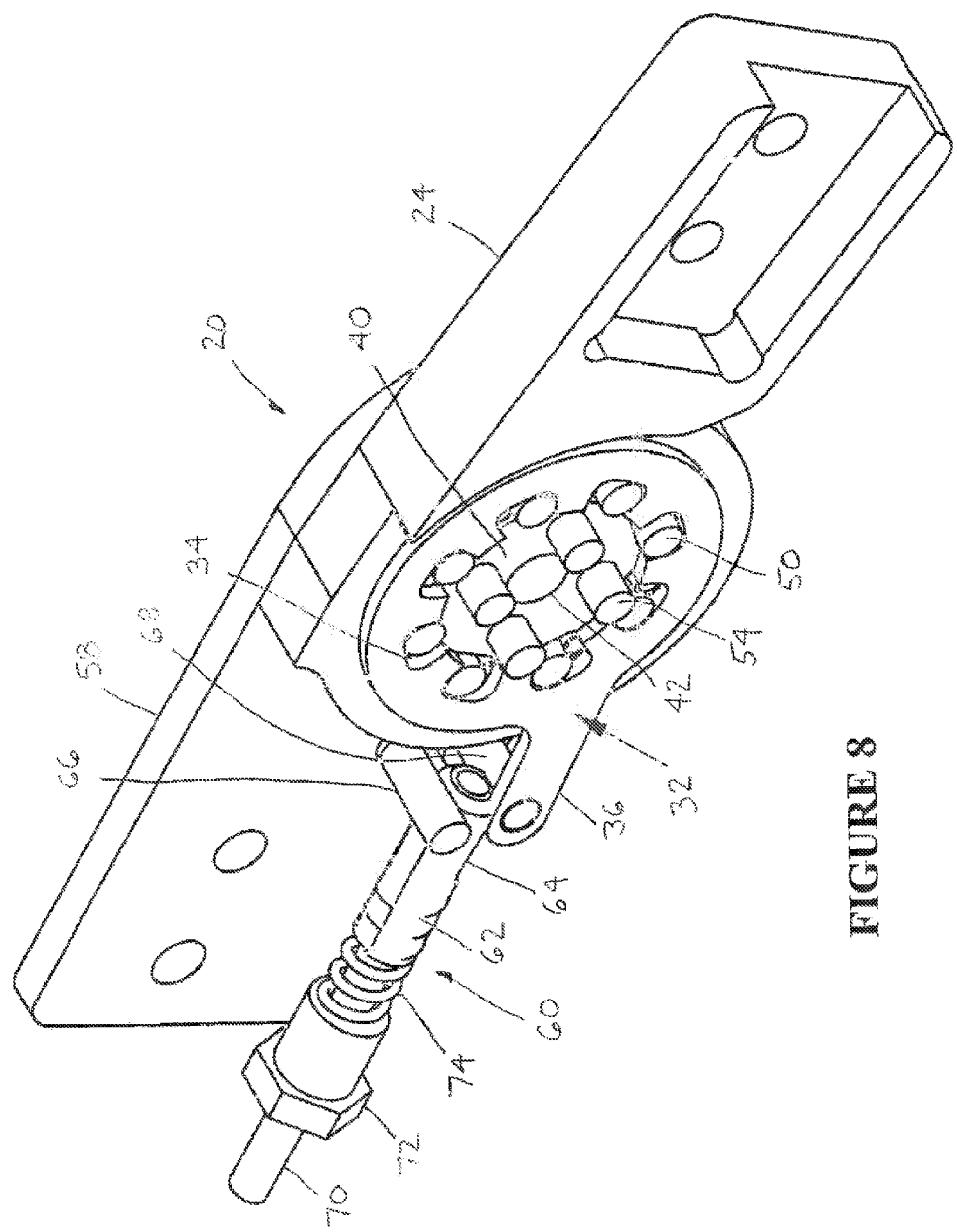
FIG. 8 is a perspective front view of the preferred embodiment of the mechanical joint illustrated in FIGS. 1 through 7.

Referring now to FIG. 8, a perspective front view of the preferred mechanical joint 20 is illustrated. As shown in FIG. 8, the preferred mechanical joint 20 comprises distal race 24, release plate 32, release plate notches 34, release plate arm 36, iris 40, pivot screw aperture 42, roller bearing pins 50, drive pins 54, proximal plate 58, and cable pull assembly 60. The preferred cable pull assembly 60 comprises cable pull actuator 62, actuator ramp 64, cable pull pin 66, actuator pin 68, cable pull connector 70, guide screw 72 and return spring 74.

Figure 9:
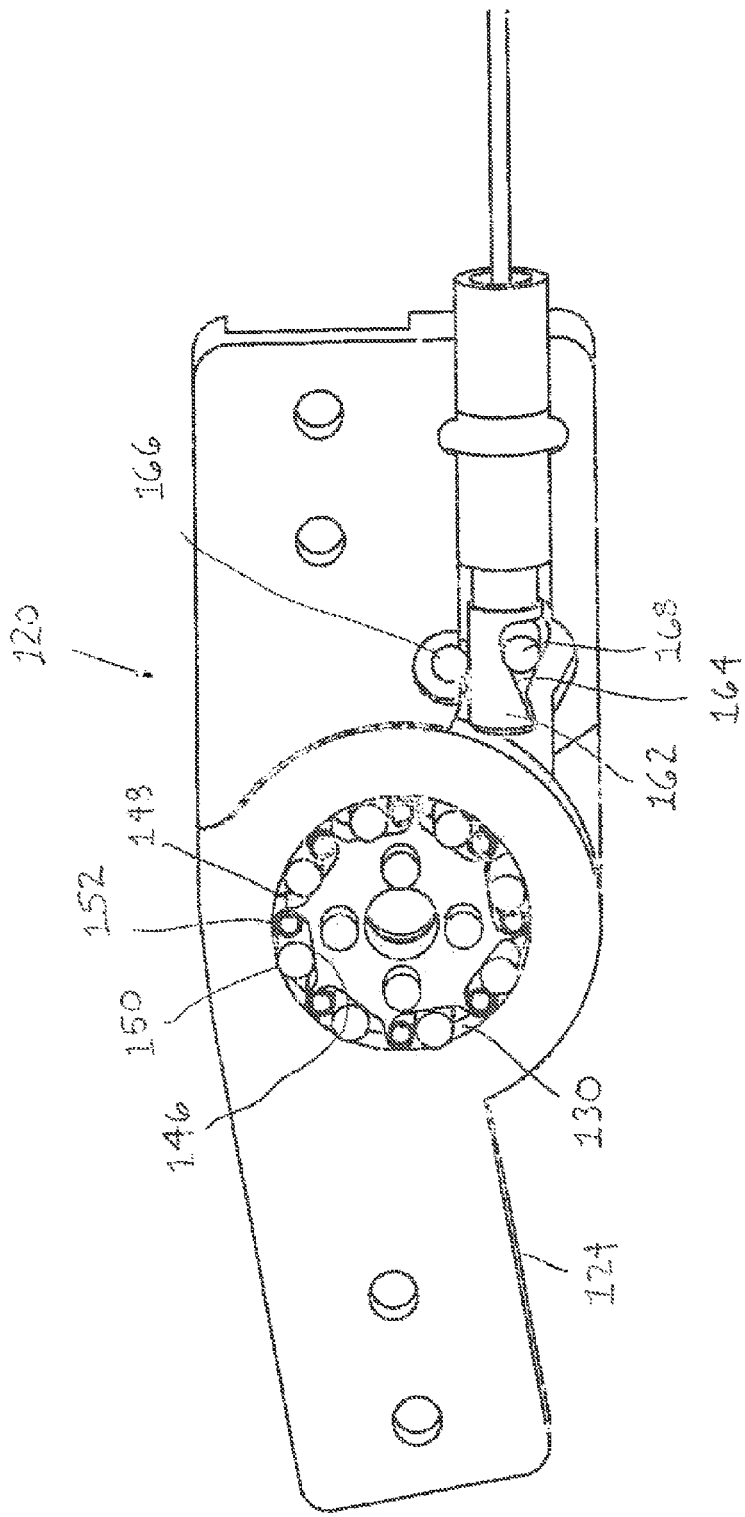
FIG. 9 is a perspective rear view of a first alternative embodiment of the mechanical joint in accordance with the present invention in a locked position.

Referring now to FIG. 9, a perspective rear view of a first alternative embodiment of the mechanical joint in accordance with the present invention is illustrated. As shown in FIG. 9, the preferred mechanical joint is designated generally by reference numeral 120. More particularly, preferred mechanical joint 120 is shown in its default mode, i.e. the locked position. As shown in FIG. 9, when preferred mechanical joint 120 is in the locked position, the each of the preferred resilient tubes 152 urges a roller bearing pin 150 away from the roller pocket 148 and outwardly along roller ramp 146 so as to come into bearing contact with round race 130 of distal race 124. In the locked position, the return spring urges cable pull actuator 162 toward the release plate such that the actuator pin 168 is relatively close to cable pull pin 166 and adjacent to the narrow or shallow portion of the actuator ramp 164.

Figure 10:
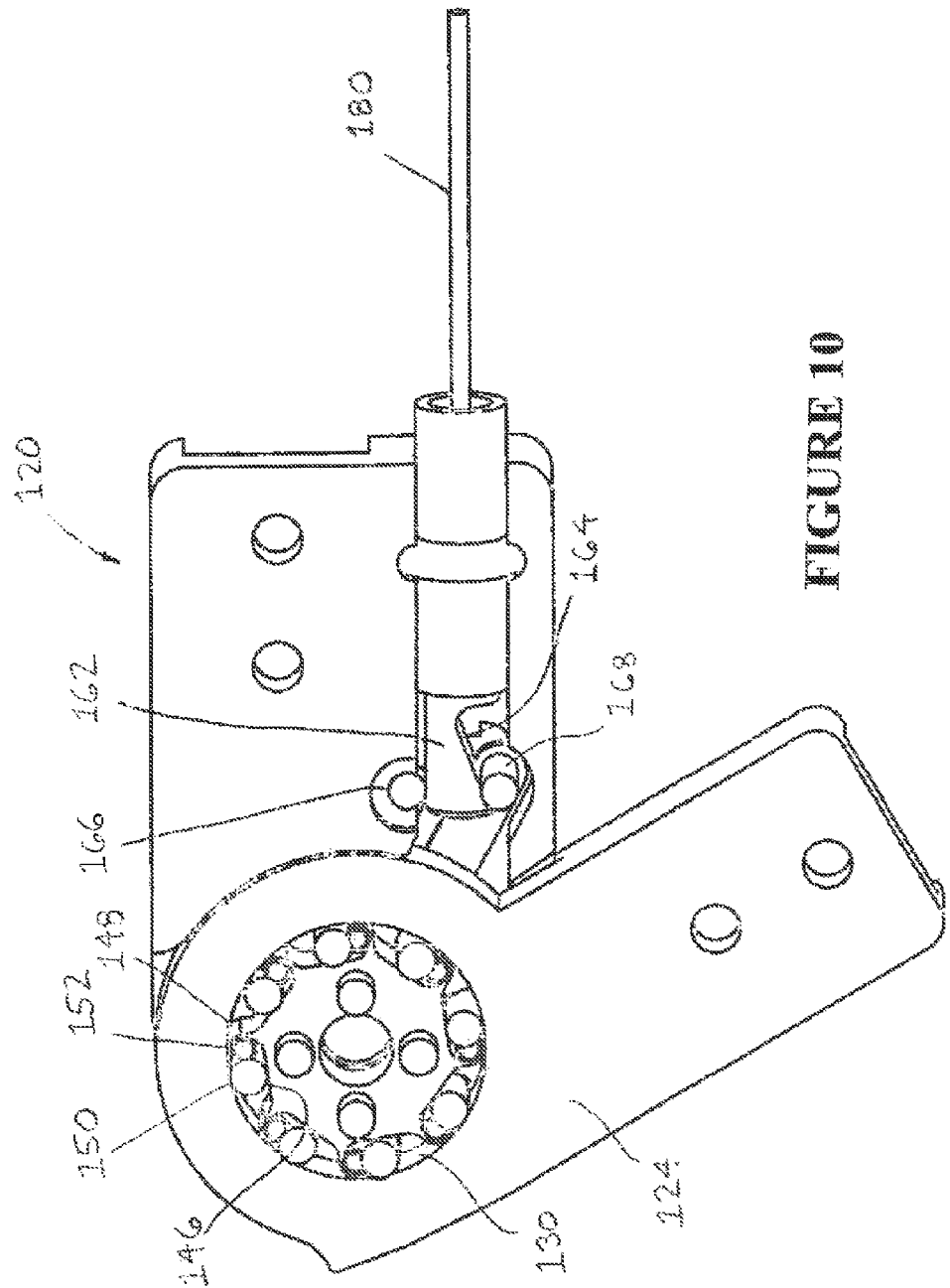
FIG. 10 is a perspective rear view of the first alternative embodiment of the mechanical joint illustrated in FIG. 9 shown in an unlocked position.

Referring now to FIG. 10, a perspective rear view of preferred mechanical joint 120 is illustrated. More particularly, preferred mechanical joint 120 is shown in an unlocked position. As shown in FIG. 10, in the unlocked position, the actuator cable 180 is pulled in a direction away from the release plate and the actuator 162 is urged against the return spring. As a result of the movement of actuator 162 away from the release plate, the actuator pin 168 is disposed adjacent to the wider or deeper portion of actuator ramp 164 and relatively far from the cable pull pin 166. As the actuator pin 168 moves away from cable pull pin 166, the release plate is rotated so as to urge each roller bearing pin 150 inwardly along roller ramp 146 against a resilient tube 152. As each roller bearing pin 150 is moved inwardly along roller ramp 146 and resilient tubes 152 are compressed, the roller bearing pins are no longer in bearing contact with round race 130 of distal race 124 such that the distal race is able to move relative to the proximal body about the pivot point defined by the pivot screw. In a preferred embodiment of mechanical joint 120, the joint is adapted to be unlocked with approximately 0.3" of linear movement of the cable pull assembly. In another preferred embodiment of the mechanical joint 120, the joint is adapted to be unlocked with approximately 3° of angular movement of the release plate.

In operation, several advantages of the preferred embodiments of the invention are achieved. For example, the preferred embodiments of the mechanical joint are adapted to provide an apparatus and a method for an orthotic and prosthetic joint that is lighter in weight and smaller in size. The preferred embodiments of the invention also provide an apparatus and a method that demonstrates improved performance and functionality. More particularly, the preferred embodiments of the invention provide an apparatus and a method for an orthotic and prosthetic joint having a release mechanism that travels a shorter distance than conventional joints and requires no external release mechanism such as a ratcheting device. The preferred embodiments of the invention provide an apparatus and a method that is more cosmetically pleasing than conventional joints. The preferred embodiments of the invention also provide an apparatus and method that permits the user to wear the joint on both sides of the user's anatomical joint, e.g. the lateral and medial sides of the user's anatomical knee joint. Further, the preferred embodiments or the invention provide an apparatus and method that reduces or eliminates noise during operation and reduces the profile of the mechanical joint.

Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. A mechanical joint being adapted to for use on a user's anatomical joint, said anatomical joint having a proximal area, a distal area, a lateral side and a medial side, and said mechanical joint comprising:
    (a) a proximal body for, said proximal body being disposed adjacent to the proximal area of the user's anatomical joint;
    (b) a distal race for, said distal race being disposed adjacent to the distal area of the user's anatomical joint;
    (c) a release plate, said release plate being substantially disposed in the proximal body;
    (d) an iris, said iris being substantially disposed in the proximal body;
    (e) at least one roller bearing pin, said roller bearing pin being substantially disposed in the proximal body;
    (f) a resilient tube, said resilient tube being substantially disposed in the proximal body;
    (g) a drive pin, said drive pin being substantially disposed in the proximal body;
    (h) a pivot screw, said pivot screw being adapted to pivotally connect the proximal body and the distal race; and (i) a cable pull assembly, said cable pull assembly being adapted to permit the distal race and the proximal body to move relative to each other.

2. The mechanical joint of claim 1 wherein the distal race comprises a round race.

3. The mechanical joint of claim 2 wherein the roller bearing pins are adapted to be in bearing contact with the round race.

4. The mechanical joint of claim 1 wherein the iris comprises a plurality of roller ramps.

5. The mechanical joint of claim 1 wherein the iris comprises a plurality of roller pockets.

6. The mechanical joint of claim 1 wherein the cable pull assembly comprises a cable pull actuator.

7. The mechanical joint of claim 6 wherein the cable pull actuator comprises an actuator ramp.

8. The mechanical joint of claim 7 wherein the cable pull assembly comprises an actuator pin.

9. The mechanical joint of claim 8 wherein the actuator pin bears against the actuator ramp.

10. The mechanical joint of claim 1 wherein the cable pull assembly comprises a cable pull connector.

11. The mechanical joint of claim 1 wherein the cable pull assembly comprises a guide screw.

12. The mechanical joint of claim 1 wherein the cable pull assembly comprises a return spring.

13. The mechanical joint of claim 1 wherein the cable pull assembly is adapted to rotate the release plate.

14. The mechanical joint of claim 1 further comprising a proximal plate, said proximal plate being disposed adjacent to the proximal body.

15. The mechanical joint of claim 1 further comprising a default mode that is locked.

16. The mechanical joint of claim 1, wherein the joint is adapted to be unlocked with approximately 0.3" of linear movement of the cable pull actuator.

17. The mechanical joint of claim 1 wherein the joint is adapted to be unlocked with approximately 3° of angular movement of the release plate.

18. The mechanical joint of claim 1 wherein the joint has a narrow profile.

19. The mechanical joint of claim 1 wherein the joint has a profile that is approximately 0.5".

20. The mechanical joint of claim 1 wherein the joint may be worn on both the lateral or medial side of the user's joint.

\* \* \* \* \*